United States Patent [19]

Goto et al.

[11] Patent Number: 4,719,212

[45] Date of Patent: Jan. 12, 1988

[54] THERAPEUTIC AGENT FOR MEMORY DISTURBANCE

[75] Inventors: Masayoshi Goto, Tokyo; Nobutaka Demura, Kawagoe; Takashi Sakaguchi, Tokorazawa, all of Japan

[73] Assignee: Hoechst Aktiengesellschaft, Frankfurt am Main, Fed. Rep. of Germany

[21] Appl. No.: 948,444

[22] Filed: Dec. 29, 1986

Related U.S. Application Data

[63] Continuation of Ser. No. 783,080, Oct. 2, 1985, abandoned.

[30] Foreign Application Priority Data

Apr. 5, 1985 [JP] Japan ................................ 60-71188

[51] Int. Cl.$^4$ .............................................. A61K 31/52
[52] U.S. Cl. .................................................. 514/263
[58] Field of Search ........................................ 514/263

[56] References Cited

U.S. PATENT DOCUMENTS 4,289,776 9/1981 Mohlr et al. ..................... 514/263

OTHER PUBLICATIONS

Negwer, "Organisch–Chemische Arzneimittel Und Ihre Synonyma", Akademie–Verlag, 1978.

Primary Examiner—Stanley J. Friedman
Attorney, Agent, or Firm—Finnegan, Henderson, Farabow, Garrett and Dunner

[57] ABSTRACT

A therapeutic agent for memory disturbance containing 1,2,3,6-tetrahydro-3-methyl-1-(5-oxohexyl)-7-propyl-purine-2,6-dione as its active ingredient and a method for treating a patient suffering from memory disturbance with such a therapeutic agent.

10 Claims, 2 Drawing Figures

THERAPEUTIC AGENT FOR MEMORY DISTURBANCE

This application is a continuation of application Ser. No. 783,080, filed Oct. 2, 1985, now abandoned.

FIELD OF THE INVENTION

The present invention relates to a therapeutic agent for memory disturbance, and more particularly, to a therapeutic agent for memory disturbance containing 1,2,3,6-tetrahydro-3-methyl-1-(5-oxohexyl)-7-propyl-purine-2,6-dione (hereinafter referred to as propentofylline) as its active ingredient.

PRIOR ART

Recently, senile diseases such as dementia associated with memory disturbance have become a big medical and social problem as the average span of life has grown. Up to now, however, there is almost no drug that is capable of effectively controlling them, and development of such drug is urgently desirable.

PROBLEMS TO BE SOLVED BY THE INVENTION

It is an object of the present invention to provide a therapeutic agent for cerebral disturbance, particularly for memory disturbance to meet such requirement. Cerebral disturbance as used herein means both the one primarily caused by the nervous system including glia cells and the one by the cerebrovascular system. Dementia as used herein means diseases manifesting psychological and physical symptoms as set forth below.

Dementia is classified into two large types. One is Alzheimer's dementia which is a disease unknown for its cause and with cerebral nervous cells impaired. The dementia of Alzheimer's type is a progressive disease in which rapidly aggravating amnesia, disorientation for time and place and depression will be observed. When the disease has been further progressed, the patient becomes highly demented and understanding of speech and ability of expression are impaired. The second type is cerebrovascular dementia caused by cerebrovascular impairment.

As stated above, the dementia patients present symptoms such as loss of intellectual capacity, disturbance of abstractive thinking, aphasia, astasia-abasia and agnosia. Disturbance of their fundamental functions lies in disturbances of the form of memory or the ability of developing retained memory.

As a result of basic research carried out for years to develop therapeutic agents effective for memory disturbance observed in dementia patients, we have found that propentofylline is highly effective for memory disturbance.

MEANS FOR SOLVING THE PROBLEMS

Propentofylline which is used as the active ingredient in the therapeutic agent for memory disturbance according to the present invention is chemically 1,2,3,6-tetra-hydro-3-methyl-1-(5-oxohexyl)-7-propyl-purine-2,6-dione and has the structural formula shown below.

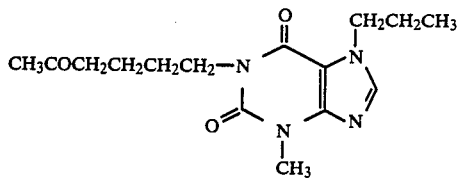

On the basis of pharmacological studies done up to now, propentofylline is known to have (1) a cerebral vasodilating activity and (2) an activity increasing cerebral blood flow. The two pharmacological activities are described in U.S. Pat. No. 4,289,776 corresponding to Canadian Pat. No. 1 075 690. Several ameliorants for cerebral circulation and metabolism have recently been developed, some of which have cerebral vasodilating activities and activities increasing cerebral blood flow. Some of the developed agents have been reported for the dementia-controlling effect. But there has been produced no general theory connecting cerebral vasodilating activities and activities increasing cerebral blood flow with effectiveness for dementia. Ameliorant for cerebral circulation and metabolism is the general term covering a variety of pharmacologically active agents to which the cerebral metabolism-activating agents, the cerebral vasodilators and the platelet aggregation inhibitors belong. Examples of the cereberal metabolism-activating agents are citicoline, meclofenoxate hydrochloride, solcoseryl, ifenprodil tartrate, cinepazide maleate, pyritinol hydrochloride bencyclane fumarate and calcium hopantenate. As cerebral vasodilators are known, in addition to ifenprodil tartrate, cinepazide maleate and bencyclane fumarate, dihydroergotoxin, nicardipine hydrochloride, pentoxifylline, cinnarizine and vinpocetine. As platelet aggregation inhibitors are used O-acetylsalicylic acid, sulfinpyrazone, dipyridamole and ticlopidine hydrochloride. Some of these drugs have been reported to be effective for dementia caused by memory disturbance but the relation between the effectiveness for dementia and other pharmacological profiles has not been established so far. Therapeutic effect of propentofylline for memory disturbance, accordingly, is not based upon the pharmacological activities described in U.S. Pat. No. 4,289,776 and Canadian Pat. No. 1 075 690, but seems to be on entirely independent pharmacological activities.

The toxicity of propentofylline used in the invention is so low that consecutive administrations may be applied. Acute toxicity ($LD_{50}$) is 375 mg/kg in male mice by intraperitoneal administration and 199 mg/kg in male rats by intraperitoneal administration.

According to the invention propentofylline may be used as an active ingredient for the treatment of humans or, particularly mammalian, animals.

Pharmacological activities of propentofylline suggesting that it will be effective for the control of memory disturbance in dementia patients will be described in details below by means of the experimental results.

EXPERIMENT 1

In general, memory formation is thought to be composed of the following three processes: At first, a memory acquiring process in which a given state of things is consolidated by learning, next comes retention of the memory, and then there is a retrieval process by which the memory is developed as needed.

In order to examine the effect of propentofylline on memory, an experiment was carried out of passive avoidance task in male ICR mice. Combination of passive avoidance task and memory disturbance caused by cycloheximide, which is an experimental method commonly employed (cf. Naoki Yamazaki et al.: Jap. J. Psychopharmacol. 3, 127 (1983)), will be described below. The apparatus used for the experiment is a plastic box 24 cm in height, 20 cm in width and 23 cm in length with a floor of electrifiable grid. There is placed a platform 8 cm in length, 8 cm in width and 1.5 cm in height at a corner of the floor grid. When a mouse is placed into the box and given an electric shock at a current strength of 0.3 mA for approximately 3 seconds, the mouse escapes onto the platform. Then, after a nonshock period of 8 seconds, it is again given the electric shock for approximately 5 seconds. This process forms memory of aversion in the mouse, thereby establishing passive avoidance learning of electric shock given when it moved off the platform. The learning is judged as established when the mouse placed on the platform just after the training does not move off the platform for 30 seconds or longer.

The main test to observe if the mouse retains the memory of aversion is carried out at appropriate days after the training is completed. Memory retention is calculated according to the equation given below.

Memory retention (%) =

$$\frac{\text{Number of animals having not moved off the platform for 3 min. or longer}}{\text{Total number of animals tested}} \times 100$$

In order to induce memory disturbance in mice, a solution of cycloheximide dissolved in physiological saline is administered intraperitoneally at a dose of 120 mg/kg 15 minutes prior to the training. The mice are trained by giving electric shock in the same way as above.

Memory retention in 30 control animals was maintained at a level of about 40% during the experiment. The control animals have relatively stable memory retention. On the other hand, the cycloheximide-treated group of 59 animals had memory retention at a level of 12% on the first day after the training, which is statistically different at a level of significance of 5%. This low level of memory retention on the first day was gradually recovered with elapse of days to the level in the control animals on the 10th day. The results are graphically shown in FIG. 1. In FIG. 1 the ordinate represents memory retention (%), the abscissa days after administration of cycloheximide, the solid line the results with the control group (non-cycloheximide-treated group), the dotted line the results with the experiment group (cycloheximide-treated group) and figures in the parenthesis number of the animals subjected to the experiment. It is evident from FIG. 1 that administration of cycloheximide does not inhibit memory consolidation and retention processes but does memory retrieval process temporarily.

Examination was made on improvement of the disturbed memory retrieval process in mice with propentofylline. The test of memory retention was carried out 24 hours after the training with propentofylline administered 30 min. prior to the test. Results of the experiment are shown in Table 1. It was observed that propentofylline has an improving effect on the disturbed memory retrieval process even at a low dose of 15 mg/kg and a remarkably improving effect at a higher dose of 30 mg/kg. The results demonstrate that propentofylline improves the disturbed memory retrieval process.

TABLE 1

| Experiment group | Dose of propentofylline (mg/kg) | Number of animals | Memory retention (%) |
|---|---|---|---|
| Control (physiol. saline + physiol. saline) | — | 46 | 54 |
| Cycloheximide + physiol. saline | — | 44 | 11++ |
| Cycloheximide + propentofylline | 7.5 | 29 | 31 |
| Cycloheximide + propentofylline | 15 | 27 | 33* |
| Cycloheximide + propentofylline | 30 | 35 | 40** |

(Notes)
++Different from the control group at a level of significance of 1%
*, **Different from the (cycloheximide + physiol. saline) group at a level of significance of 5% or 1%, respectively

EXPERIMENT 2

Examination was made whether or not the disturbance of retrieval process induced with cycloheximide was improved when propentofylline was administered prior to training. As in Experiment 1, training was carried out using male ICR mice which were intraperitoneally treated with propentofylline 30 min. prior to the training. The test of memory retention was made 24 hours after the training. Results of the experiment are shown in Table 2. Propentofylline at 15 mg/kg or 30 mg/kg improved the reduction in memory retention induced with cycloheximide. The results indicate that administration of propentofylline prior to training also improves disturbance of the memory retrieval process induced with cycloheximide.

TABLE 2

| Experiment group | Dose of propentofylline (mg/kg) | Number of animals | Memory retention (%) |
|---|---|---|---|
| Control (physiol. saline + physiol. saline) | — | 30 | 47 |
| Physiol. saline + cycloheximide | — | 59 | 12++ |
| Propentofylline + cycloheximide | 7.5 | 14 | 29 |
| Propentofylline + cycloheximide | 15 | 37 | 35* |
| Propentofylline + cycloheximide | 30 | 35 | 37** |

(Note)
++Different from the control at a level of significance of 1%
*, **Different from (physiol. saline + cycloheximide) group at a level of significance of 5% or 1%, respectively

EXPERIMENT 3

After carrying out training of the learning in the same way as in Experiment 1 using male ICR mice, observation was made of the effect of propentofylline on memory improvement. Scopolamine hydrobromide was intraperitoneally administered in the mice subjected to the passive avoidance task in order to induce memory disturbance. Propentofylline was intraperitoneally administered 15 min. prior to the test of memory retention. Measurement of memory retention in the test was made on the time until the mouse placed on the platform moved off up to the maximum of 180 seconds. Statistical analysis was made by two-sample rank-order test method (Mannwhitney U-test).

The period of time during which the mouse remains on the platform is much reduced after administration of scopolamine hydrobromide at a doese of 3 mg/kg, which indicates that scopolamine hydrobromide induces memory disturbance. This finding is well known (R. Cumin et al.: Psychopharmacology 78, 104 (1982)). Intraperitoneal administration of propentofylline (50 and 70 mg/kg respectively) caused that the mouse remained for a significantly longer period of time on the platform. The results indicate that the memory disturbance induced with scopolamine hydrobromide is recovered by propentofylline. The experimental results are shown in Table 3.

TABLE 3

| Experiment group | Dose of propentofylline (mg/kg) | Number of animals | Time remaining on platform (center value, sec.) | Measured range (sec.) |
| --- | --- | --- | --- | --- |
| Control | — | 10 | 180 | 133–180 |
| Scopolamine | — | 10 | 16 | 5–180 |
| Propentofylline + scopolamine | 30 | 10 | 48 | 7–180 |
| Propentofylline + scopolamine | 50 | 19 | 126* | 3–180 |
| Propentofylline + scopolamine | 75 | 10 | 180* | 95–180 |

(Note)
*Different from the scopolamine group at a level of significance of 5%

EXPERIMENT 4

Examination was made on the effect of propentofylline improving the learning and memory using the conditioned avoidance method. By the method, observation can be made of ability of learning and memory by means of the response to presentation of light and noise. The method allows observation of progress of learning and memory with elapse of days. Typical of the method is the Shuttle box method.

Examination was made of the effect of propentofylline on learning and memory by means of the Shuttle box method using male spontaneously hypertensive (SH) rats of 12 months old. A Shuttle box was employed as the experimental equipment. The Shuttle box is a box 26 cm in height, 44 cm in width and 24 cm in length with a floor of iron grid in which current can be delivered. The box is partitioned at the center by a plate 3 cm in height. When a rat moves from one room to the other, it must jump over the barrier plate.

Experimental procedures are as follows: A SH-rat is placed in the Shuttle box and given stimulus conditions of noise from a speaker and light from an electric lamp for 7.5 seconds. If the rat does not move to the next room over the plate at the center during the presentation period, electric stimulus is given to the extremities for 7.5 seconds. If the rat moves to the next room during the subjection of stimulus conditions, it can avoid the electric stimulus. This procedure was repeated 25 times in a rat to form one trial. When the rat took the avoidance task moving to the next room during the subjection of noise and light conditions, it was taken as right response. Estimation of the learning and memory was made on each rat in each trial according to $$\text{Ratio of right response (\%)} = \frac{\text{Number of right response} \times 100}{25}$$

Two-sample rank-order test was employed for statistical analysis.

The learning was given rats at a rate of one trial per day or five trials per week. The control group of 10 animals orally received water at a dose of 0.4 ml/100 g body weight and the experiment group of 11 animals propentofylline at a dose of 25 mg/kg. Results of the experiment are graphically shown in FIG. 2, in which the ordinate represents ratio of the right response (%), the abscissa number of the trials, the dotted line results with the control group (non-propentofylline-treated group) and the solid line results with the experiment group (propentofylline-treated group). Figures in the parenthesis respectively indicate the number of rats used in the experiment. The mark * attached to the solid line means that there is a difference from the control group at a level of significance of 5%, and the mark ** means that there is a difference from the control group at a level of significance of 1%. As clearly seen from FIG. 2, whereas there was observed in the control group almost no improvement of the learning avoiding electric stimulus, the ratio of right response in the rats receiving propentofylline was gradually increased with an increase in repetition of the trial. The results indicate that propentofylline has an effect improving learning and memory.

The results given above demonstrate that propentofylline is effective in the therapy of memory disturbance associated with dementia.

Clinical doses of propentofylline in humans are in the range between 50 or 100 and 1,500 mg per day depending upon route of administration. These dosages are administered in dosage units. Dosage units for oral administration in general contain 50–800, preferably 100–500 mg of propentofylline. Dosage units for rectal administration in general contain from 100–1,000, preferably from 150 to 600 mg of propentofylline and dosage units of injectable preparations contain in general from 25 to 200, preferably from 50 to 150 mg of propentofylline.

Route of administration may be intravenous, intramuscular, oral or rectal. Intravenous drip infusion may be applied for the intravenous administration in addition to the intravenous injection.

Pharmaceutical preparations containing propentofylline are prepared by conventional methods using conventional excipients or additives or both.

As injectable preparations may be used, for example, a powdered preparation for injection. In this case, the preparation can be produced by dissolving the drug in water in admixture with one or more appropriate water-soluble excipients such as mannitol, sucrose, lactose, maltose, glucose or fructose, dividing into vials or ampules after lyophyllizing and sealing.

The preparations for oral use may be conventional tablets, capsules, granules, fine granules, powders, and additionally enteric coated preparations.

In order to produce the enteric coated preparations, the drug, in admixture with excipients such as mannitol, sucrose, lactose, maltose, starch, silicic anhydride and calcium phosphate, lubricants such as talc and magnesium stearate, binders such as carboxymethylcellulose, methylcellulose, gelatine and arabic gum and disintegrators such as calcium carboxymethylcellulose as needed, is formed into tablets, granules, fine granules or the like, followed by coating with one or more enteric coating materials such as cellulose acetate phthalate, hydroxypropylmethylcellulose phthalate, hydroxypropylmethylcellulose acetylsuccinate, polyvinylalcohol phthalate, styrene-maleic anhydride copolymer, styrene-maleic acid copolymer, methyl methacrylate-methyl acrylate copolymer and methyl acrylate-methacrylic acid copolymer, as well as with coloring agents such as titanium oxide as needed to obtain a pharmaceutical preparation. In addition, the enteric coated granules or fine granules thus obtained may be filled in capsules to form a capsule preparation.

It is also feasible that capsules prepared by a conventional method are subjected to coating to make them enteric or enteric capsules are prepared using capsules produced from the above-mentioned enteric coating materials alone or in admixture with gelatine.

Rectal preparations can be formed by homogeneously blending the drug with a melt obtained by warming a lipophilic base such as cacao butter or a semisynthetic base by mixing a fatty acid triglyceride with a fatty acid monoglyceride or diglyceride in various proportions or a hydrophilic base such as polyethylene glycol or glycerogelatine and molding the blend.

Examples of the invention will be given below.

EXAMPLE 1

To 20 g of propentofylline and 16 g of sodium chloride was added distilled water to a total volume of 2,000 ml. The solution was sterile filtered through a 0.22 micron-millipore filter and divided into 5-ml portions in ampules 5 ml in volume, which were sealed and sterilized in an autoclave to produce injectable preparations.

EXAMPLE 2

To 500 g of propentofylline were added 250 g of lactose, 150 g of corn starch, 150 g of calcium carboxymethylcellulose, 42 g of talc, 5 g of magnesium stearate and 3 g of silicic anhydride. The mixture was formed into tablets. Separately, in 500 g of water were dispersed 40 g of hydroxypropylmethylcellulose, 2 g of polyethylene glycol 6000, 3.5 g of titanium oxide and 3 g of talc. The tablets obtained above were coated with the dispersion to give tablets containing 115 mg of propentofylline per tablet.

Figure 1:
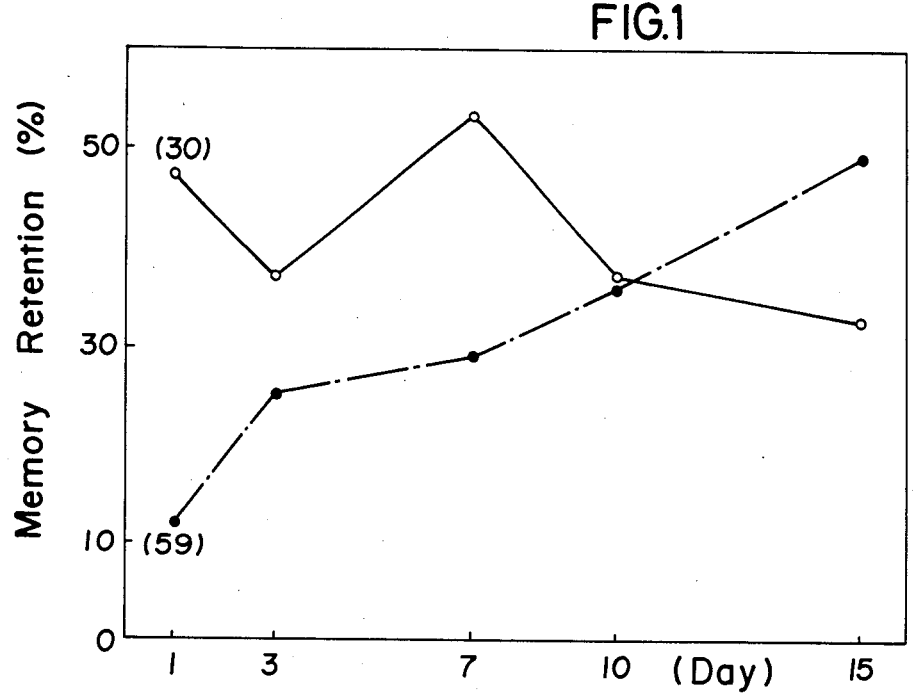
FIG. 1 is a graph representing memory retention of mice treated with cycloheximide.
Figure 2:
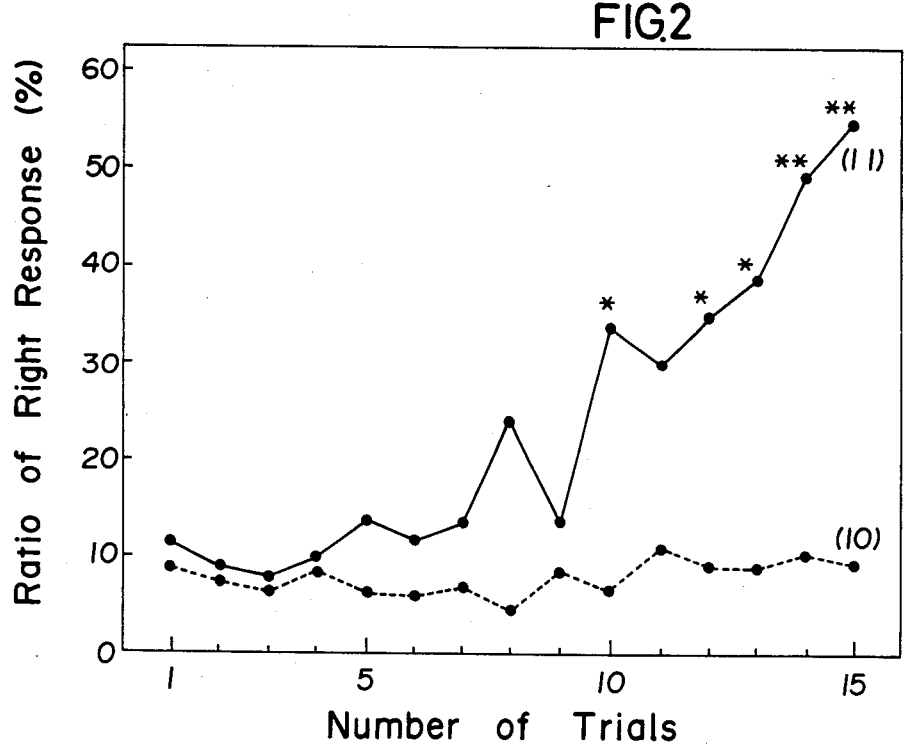
FIG. 2 is a graph representing conditioned avoidance learning of SH-rats when treated with propentofylline.

We claim:

1. A method for treating a patient suffering from Alzheimer's dementia which comprises administering to such patient a pharmaceutical composition comprising as the essential ingredient an effective amount of 1,2,3,6-tetrahydro-3-methyl-1-(5-oxohexyl)-7-propyl-purine-2,6-dione.

2. A process as claimed in claim 1, wherein the patient is a human being.

3. A process as claimed in claim 1, wherein the patient is a mammalian animal.

4. A process as claimed in claim 1, wherein the amount is in the range of 100 to 1500 mg per day.

5. A method as claimed in claim 1, wherein a pharmaceutical composition in dosage unit form for oral administration containing in each dosage unit from 50 to 800 mg of 1,2,3,6-tetrahydro-3-methyl-1-(5-oxohexyl)-7-propyl-purine-2,6-dione is administered.

6. A method as claimed in claim 5, wherein a pharmaceutical composition containing from 100 to 500 mg of 1,2,3,6-tetrahydro-3-methyl-1-(5-oxohexyl)-7-propyl-purine-2,6-dione in each dosage unit is administered.

7. A method as claimed in claim 1, wherein a pharmaceutical composition in dosage unit form for rectal administration containing in each dosage unit from 100 to 1,000 mg of 1,2,3,6-tetrahydro-3-methyl-1-(5-oxohexyl)-7-propyl-purine-2,6-dione is administered.

8. A method as claimed in claim 7, wherein a pharmaceutical composition containing from 150 to 600 mg of 1,2,3,6-tetrahydro-3-methyl-1-(5-oxohexyl)-7-propyl-purine-2,6-dione in each dosage is administered.

9. A method as claimed in claim 1, wherein a pharmaceutical composition in dosage unit form for administration by injection containing in each dosage unit from 25 to 200 mg of 1,2,3,6-tetrahydro-3-methyl-1-(5-oxohexyl)-7-propyl-purine-2,6-dione is administered.

10. A method as claimed in claim 9, wherein a pharmaceutical composition containing from 50 to 150 mg of 1,2,3,6-tetrahydro-3-methyl-1-(5-oxohexyl)-7-propyl-purine-2,6-dione in each dosage unit is administered.

* * * * *